(12) United States Patent
Besek

(10) Patent No.: US 6,960,082 B2
(45) Date of Patent: Nov. 1, 2005

(54) ATRAUMATIC APPROXIMAL SPACE DILATOR

(75) Inventor: Mario Besek, Thalwil (CH)

(73) Assignee: Ivoclar Vivadent AG, Schaan (LI)

( * ) Notice: Subject to any disclaimer, the term of this patent is extended or adjusted under 35 U.S.C. 154(b) by 186 days.

(21) Appl. No.: 10/149,735

(22) PCT Filed: Dec. 4, 2000

(86) PCT No.: PCT/IB00/01788

§ 371 (c)(1),
(2), (4) Date: Jun. 12, 2002

(87) PCT Pub. No.: WO01/47428

PCT Pub. Date: Jul. 5, 2001

(65) Prior Publication Data

US 2002/0192619 A1 Dec. 19, 2002

(30) Foreign Application Priority Data

Dec. 24, 1999 (CH) .............................................. 2379/99

(51) Int. Cl.[7] ................................................. A61C 7/00
(52) U.S. Cl. ....................................... 433/39; 433/148
(58) Field of Search ................................. 433/148, 149, 433/39, 40, 41, 18

(56) References Cited

U.S. PATENT DOCUMENTS

| 351,065 | A | * | 10/1886 | Miller | ........................ | 433/39 |
|---|---|---|---|---|---|---|
| 427,338 | A | * | 5/1890 | Marshall | .................... | 433/149 |
| 701,799 | A | * | 6/1902 | Crenshaw | .................... | 433/39 |
| 1,456,294 | A | | 5/1923 | Arrowsmith | | |
| 1,464,532 | A | | 8/1923 | Ivory | | |
| 1,702,869 | A | | 2/1929 | Ivory | | |
| 2,288,011 | A | * | 6/1942 | Mizzy | ........................ | 433/148 |
| 2,647,351 | A | * | 8/1953 | Arnold | ........................ | 451/463 |
| 3,046,659 | A | * | 7/1962 | Tofflemire | .................... | 433/39 |
| 3,197,870 | A | * | 8/1965 | Tofflemire | .................. | 433/149 |
| 4,718,852 | A | | 1/1988 | Galler | | |
| 5,328,364 | A | * | 7/1994 | Doyle | ......................... | 433/18 |
| 5,330,353 | A | * | 7/1994 | Wavrin | ....................... | 433/39 |
| 5,378,147 | A | * | 1/1995 | Mihailowitsch | .............. | 433/19 |
| 5,380,198 | A | * | 1/1995 | Suhonen | ...................... | 433/39 |
| 5,460,525 | A | * | 10/1995 | Rashid | ....................... | 433/155 |
| 5,573,400 | A | | 11/1996 | Asher | | |
| 5,993,210 | A | | 11/1999 | Godfrey | | |
| 6,217,323 | B1 | * | 4/2001 | Liou | ........................... | 433/18 |

FOREIGN PATENT DOCUMENTS

EP  0 910 996  4/1999

* cited by examiner

*Primary Examiner*—Todd E. Manahan
(74) *Attorney, Agent, or Firm*—Merchant & Gould P.C.

(57) ABSTRACT

The invention relates to a dental device for dilating interdental spaces. The device comprises two interdental matrices that can be inserted into interdental spaces two retaining arrangements to retain the interdental matrices, and a spacer device for guiding the retaining means in parallel and for separating teeth. The device provides access to the mesial and distal tooth surfaces in the areas of the interdental spaces and prevents gingival injuries and damages to the dental enamel caused by pressure. The device can be used in prophylactic or restorative odontotherapeutical methods.

23 Claims, 3 Drawing Sheets

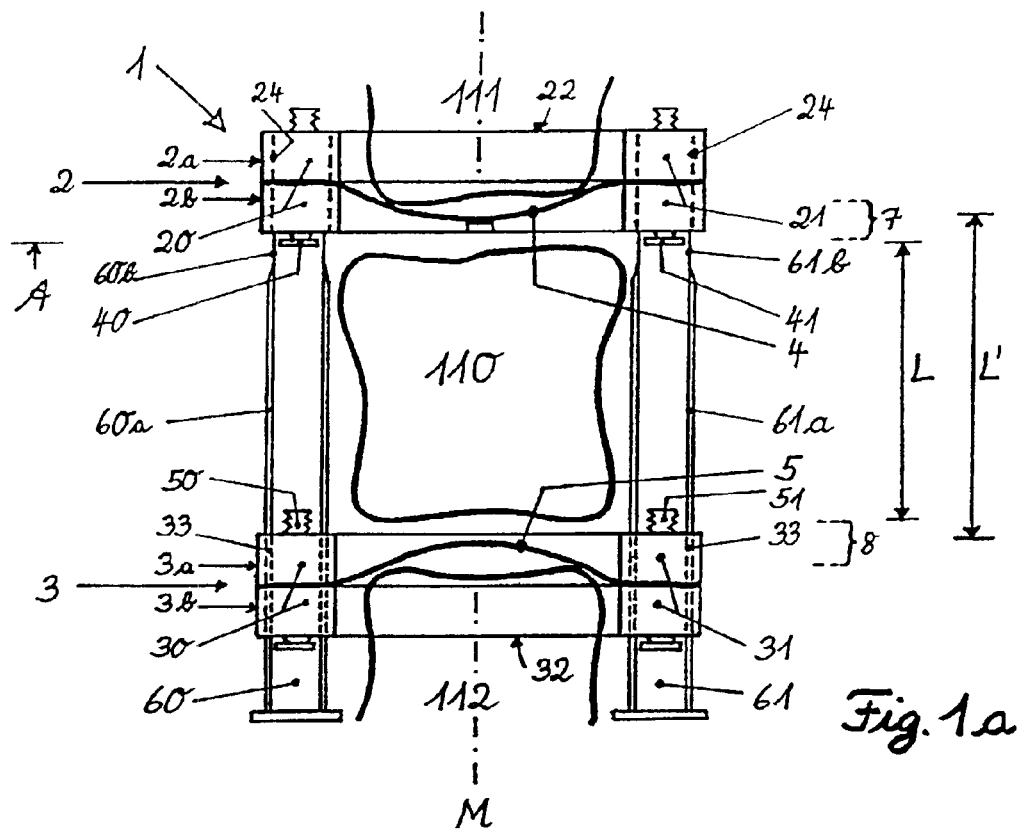
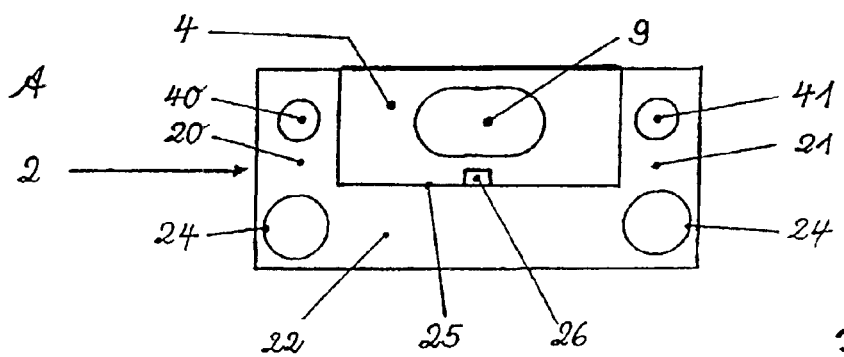

ATRAUMATIC APPROXIMAL SPACE DILATOR

TECHNICAL FIELD

The invention relates to the field of dental medicinal apparatuses. It emanates from a dental device for dilating interdental spaces in accordance with the introductory portion of the independent claim.

PRIOR ART

In the prior art such approximal space dilators are known to be in the shape of wedges. The wedge is inserted between two adjacent teeth and urges them apart by a manual force. The U.S. Pat. No. 5,573,400 discloses a wedge for a locking of a matrice for reasons of preparing teeth. After the matrice has been placed the wedge is inserted and presses the matrice by a moisture caused swelling against the tooth to be prepared.

In all cases the wedge is inserted directly between adjacent teeth, exerts a force between same and possibly presses them apart. The wedge covers, thereby, portions of the tooth side surfaces so that they are no longer accessible for the purpose of treatments. Additionally, the use of wedges is problematic because wedge edges can cause injuries of the gum and pressure increases due to small contact surfaces at the teeth leading to injuries of the dental enamel.

SUMMARY OF THE INVENTION

The invention has as object to provide a dental device for an approximal space dilation which is substantially atraumatic and allows an improved access to the interdental space. This object is met in accordance with the invention by the features of the independent claim.

The dental device of the invention comprises two interdental matrices, two retaining means for retaining same and a spacer device adapted to push the retaining means apart and to guide them for a parallel movement, whereby a distance between the interdental matrices is adjustable at the spacer device in a range of at least one tooth length up to a spacing length larger than a tooth length. Interdental matrices can be inserted in a simple way and without causing any injuries into the interdental spaces. The length of the spacer device is adjustable in such a manner that initially no force acts between the retaining means. By means of the spacer device the retaining means and the interdental matrices can be urged substantially parallel apart from each other. The interdental matrices are flexible and thus capable to conform to the shape of a tooth to such an extent that the force can be transmitted over a large, uniformly loaded surface area onto the teeth. The spacer device features typically a length for a bridging of one tooth. Due to this the interdental spaces to the adjacent teeth can be enlarged for prophylactic, preparative and other reasons. The space device may, however, also have a length for bridging several teeth, so that the dental device can be applied at teeth gaps, adjacent teeth which are in need of protection, and similar.

First examples refer to embodiments of the interdental matrices. Due to retaining means with releasable mounting devices, e.g. clamping jaws and locking screws or sliding-in slots for the interdental matrices, matrices can be very easily exchanged if so needed. By means of massive interdental matrices a largest possible tooth surface area for a transmitting of a forces onto the adjacent tooth which is to be pushed away is available. With interdental matrices having windows also the side surface of the tooth to be pushed away is accessible for tooth treatments. It is also possible to have an additional partial matrice mounted to a interdental matrice, which serves as modelling aid or separating foil during the preparing of the adjacent tooth.

Second embodiments refer to retaining means in form of U-shaped carriers with a base and sidewise mounting means for the receipt of interdental matrices. The base includes preferably a resting surface and/or a projection for a supporting of the interdental matrices. This design for the mounting ensures that the interdental matrices can easily be inserted into the interdental spaces and at the same time an effective transmittal of force onto the mounting means, the interdental matrices and the teeth.

Third embodiments refer to spacing devices with separator screws and guide pins. Preferably, two separator screws with guide pins arranged integrally at their ends are located symmetrically at both sides of the interdental matrices. By means of this the design of the dental device is very simple and the access to the interdental space is hardly curtailed.

Further embodiments, advantages and applications of the invention ensue from the dependent claims and the now following description with reference to the drawings.

BRIEF DESCRIPTION OF THE DRAWINGS

FIG. 1a illustrates a top view of a first dental device for the approximal space dilation in accordance with the invention and FIG. 1b a front view;

Same parts are given the same reference numerals in the figures.

MODES FOR CARRYING OUT THE INVENTION

Figure 2A:
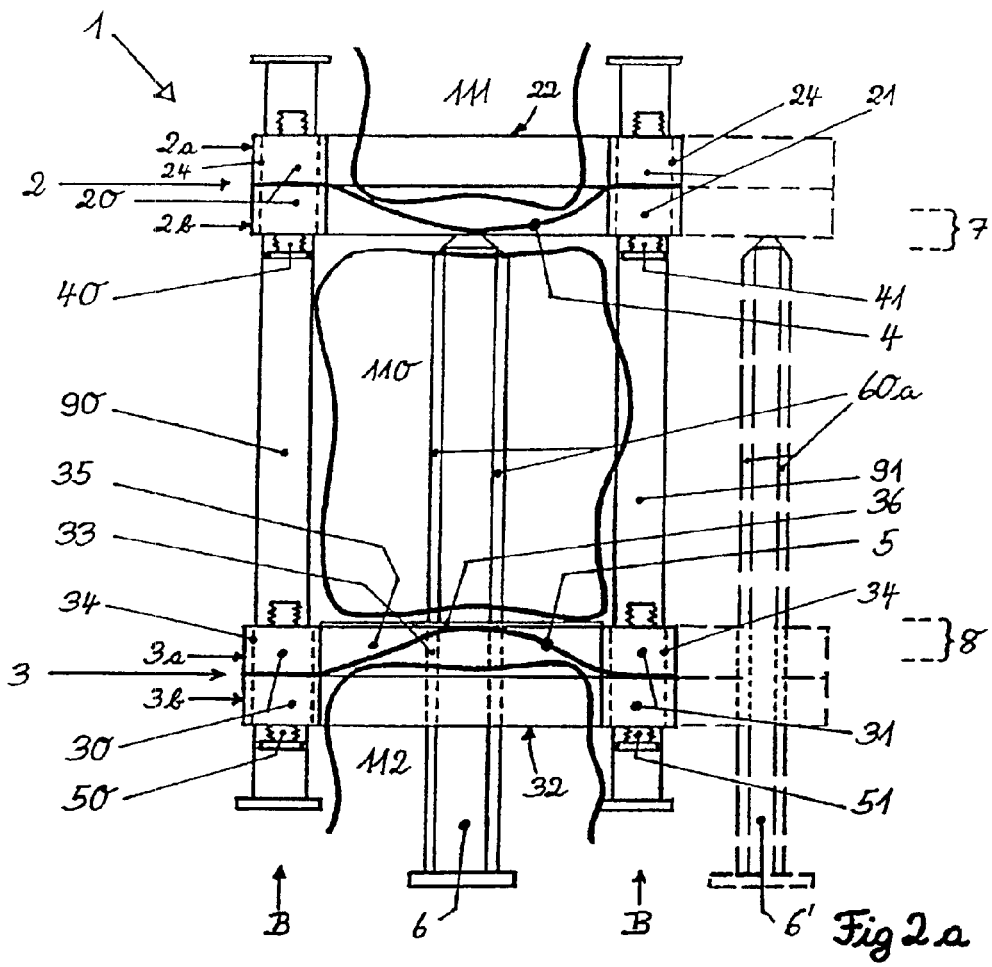
FIG. 2a illustrates a top view of a second device for the approximal space dilatation in accordance with the invention and FIG. 2b a frontview.

According to the FIGS. 1a, 1b, 2a, 2b and 3 the dental device 1 for a dilating of a interdental space 7, 8 between teeth 110, 111, 112 structured in accordance with the invention is characterized by two interdental matrices 4, 5 for an insertion into interdental spaces 7, 8, two retaining means 2, 3 for a retaining of interdental matrices 4, 5 and a spacer device 6, 6', 60, 61, 60b, 61b, 90, 91 adapted to push the retaining means 2, 3 apart and to guide them to move parallel. A distance between the interdental matrices 4, 5 is adjustable at the spacer device 6, 6', 60', 61, 60b, 61b, 90, 91 within a range of at least one up to more than one tooth length L. Below, some embodiments are disclosed.

The interdental matrices 4, 5 can be releasably mounted at the retaining means 2, 3. By means of this, worn matrices 4, 5 or matrices 4, 5 for specific applications, e.g. matrices of a different material, of various thicknesses or of different shapes may easily be exchanged, and also during an operation of the dental device 1. Generally the interdental matrices are massive. In order to improve the stability against bending they can have e.g. a reinforcing frame. A window 9 which is transparent for light of a polymerization lamp and/or for the optical range can also be foreseen. The window 9 is for instance a plastic material window 9 or a opening 9. The window 9 may be positioned centrally or at an other location. A dental treatment, e.g. a light curing, a sealing or similar may proceed through the window 10.

Figure 4:
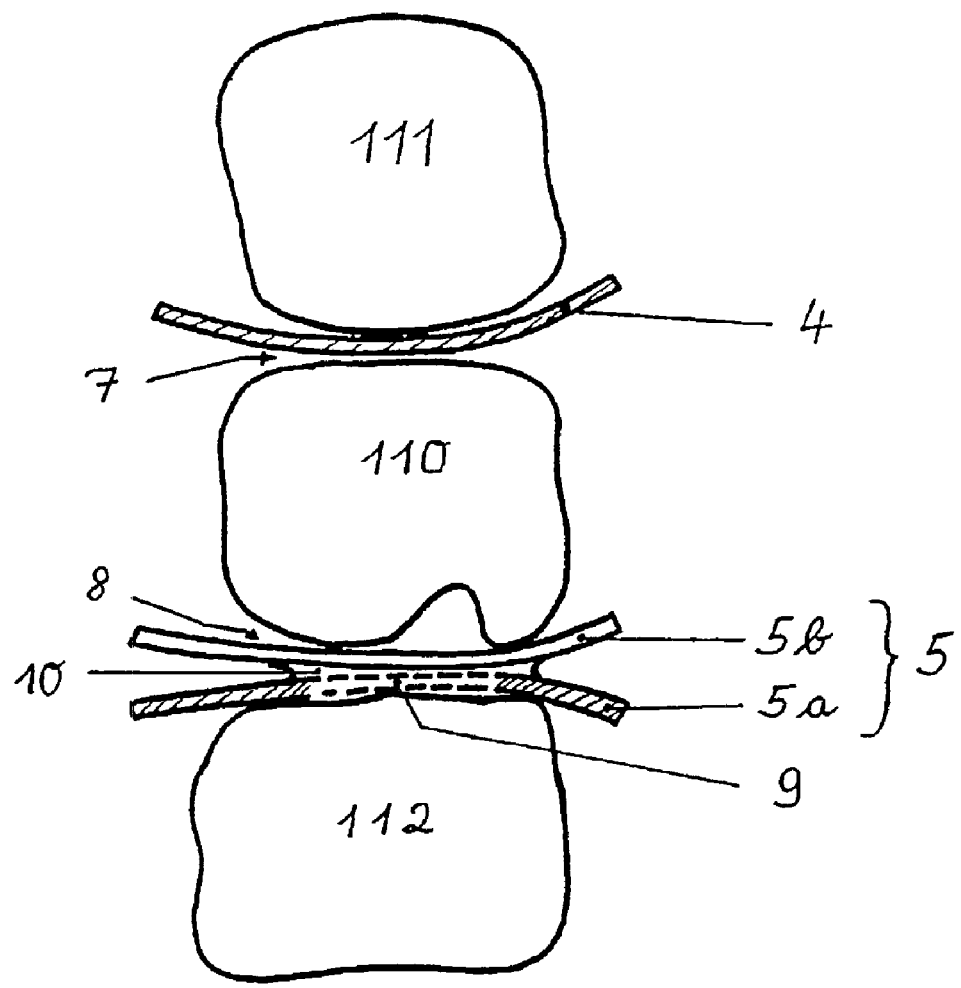
FIG. 4 illustrates an embodiment with a double-wing interdental matrice for a tooth treatment.

A further variant of the interdental matrices 4, 5 is illustrated in FIG. 4. Here, the interdental matrice 5 includes two partial matrices 5a, 5b of which a first partial matrice 5a is retained on a (not illustrated) retaining means 3 and a second partial matrice 5b is retained at the first partial matrice. The partial matrices 5a, 5b can be connected to each other by an adhesive agent. The first partial matrice 5a serves as above for the transmittal of force onto the tooth 112 which is to be pushed away. The second partial matrice 5b acts, however, as a modeling aid or separating foil during the treatment of the adjacent tooth 110. The two partial matrices 5a, 5b include advantageously a common window 9. The two partial matrices have for instance overlapping openings 9. Alternatively, such as illustrated in FIG. 4, the partial matrice 5a may have an opening 9 and the partial matrice 5b may consist of a plastic material which is transparent in the desired range of its longitudinal extent. Also other combinations, e.g. two partial matrices 5a, 5b of a plastic material can be thought of.

Important is the optical and/or mechanical accessibility to the portion of the tooth 110 to be treated in the area of the interdental space 8.

FIGS. 1a, 1b, FIGS. 2a, 2b and FIG. 3 disclose as retaining means 2, 3 U-shaped carriers 2, 3 which include a base 22, 32 and two side portion with mounting means 20, 21, 30, 31, 40, 41, 50, 51; 38, 39 for the interdental matrices 4, 5. The base 22, 32 includes advantageously a resting surface 25, 35 for a side or bottom edge support of the interdental matrices 4, 5. The base 22, 32 includes alternatively or additionally a projection 26, 36 for a supporting of the interdental matrices 4, 5 at the front or the back against a bending when the retaining means 2, 3 are pushed apart.

The mounting means 20, 21, 30, 31, 40, 41, 50, 51 can be clamping jaws 20, 21, 30, 31 with locking screws 40, 41, 50, 51 for engaging perforations in the interdental matrices 4, 5. The U-shaped carriers 2, 3 consist specifically each of two U-shaped partial carriers 2a, 2b; 3a, 3b of which the side parts or arms form the clamping jaws 20, 21, 30, 31.

The spacer device 6, 6', 60, 61, 60b, 61b, 90, 91 can include at least one separator screw 6, 6', 60, 61 and at least one guiding pin 60b, 61b, 90, 91 and the retaining means 2, 3 can include at least one threaded bore 33 for the separator screw 6, 6', 60, 61 and at least one guiding bore 24, 34 for the guiding pin 60b, 61b, 90, 91.

At the embodiment according to FIG. 1a and FIG. 1b the spacer device 60, 61, 60b, 61b includes two separator screws 60, 61 which at one end are integrally connected to a respective guide pin 60b, 61b. A first one of the retaining means 3 includes two threaded bores 33 for the separator screws 60, 61 or their threads 60a, 61a and a second one of the retaining means two guiding bores 24 for the guiding pins 60b, 61b.

Figure 2B:
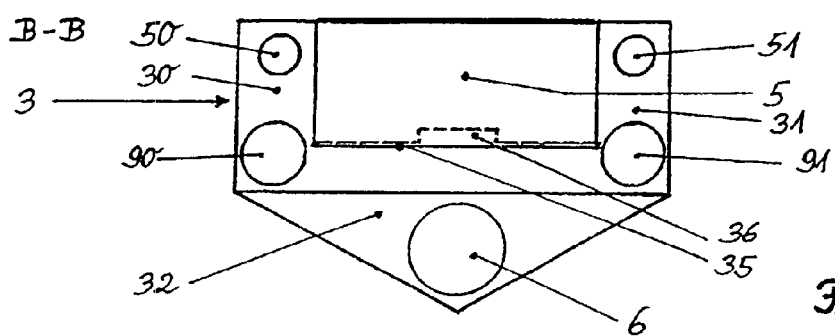

At the embodiment according to FIG. 2a and FIG. 2b the spacer device 6, 6', 90, 91 includes exactly one central separator screw 6 and two lateral guiding pins 90, 91. The arrangement of the separator screw 6, 6' and of the guiding pins 90, 91 can vary. Specifically the separator screw 6' may be also located at the side such as indicated by broken lines.

The spacer device 6, 6', 60, 61, 60b, 61b, 90, 91 can alternatively include also two separator screws 60, 61; 6, 6' and exactly one guiding pin 90; 91. Combinations of a plurality of separator screws 60, 61, 6, 6' with a plurality of guiding pins 60b, 61b, 90, 91 are also possible.

The spacer device 6, 6', 60, 61, 60b, 61b, 90, 91 is preferably arranged symmetrically relative to the interdental matrices 4, 5, i.e. that it is designed in mirror symmetry relative to a plane of symmetry M common to both retaining means. By means of this a non-canting, parallel displaceability of the retaining means 2, 3 and a uniform loading of the interdental matrices 4, 5 over their entire surface is ensured. Specifically, the at least one separator screw 6, 60, 61 and/or the at least one guiding pin 90, 91 and the corresponding at least one threaded bore 33 and/or the corresponding at least one guiding bore 24, 34 are located at a central position, i.e. in the plane of symmetry M, or in pair-wise mirror-symmetrical positions relative to the plane of symmetry M, i.e. in pair-wise equal distances at both sides of the plane of symmetry M.

The dental device 1, specifically the interdental matrices 4, 5 should consist of steel, a plastic material and/or compound materials based on carbon fibers. The dental device 1 shall not include any sharp edges and shall be sterilizable. The screws 6, 6', 60, 61, 40, 41, 50, 51 of the dental device 1 are preferably socket head cap screws.

Figure 3:
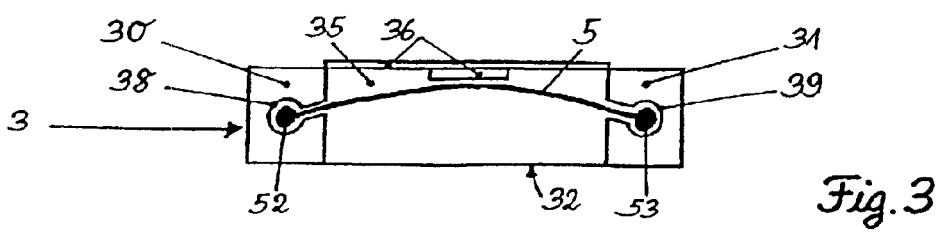
FIG. 3 illustrates an alternative mounting of an interdental matrice.

FIG. 3 illustrates an alternative embodiment of releasable mounting means 38, 39. Here, insertion slits 38, 39 for the interdental matrices 4, 5 are set in the side portions or arms of a for instance single-part carrier 30. The interdental matrice 5 includes specifically at two opposite edges thickened areas 52, 53 for the insertion into the insertion slots 38, 39. The insertion slots 38, 39 could also have not illustrated snap action locks. By these measures the insertability and exchangeability of the interdental matrices during operation are simplified still further.

By means of the dental device 1 structured in according to the invention a dental medicinal procedure encompassing the following steps can be executed: Inserting the dental device 1 whereby the interdental matrices 4, 5 are slid into different interdental spaces 7, 8; pushing the interdental matrices 4, 5 away from each other by an increasing of their distance at the spacer device 6, 6', 60, 61, 60b, 61b, 90, 91; dental treatment in the area of the spread apart interdental space 7, 8; relieving the interdental matrices 4, 5 by a decreasing their distance at the spacer device 6, 6', 60, 61, 60b, 61b, 90, 91; and removing the dental device 1 by pulling the interdental matrices 4, 5 out.

The inserting of the dental device 1 may proceed by sliding in of the interdental matrices 4, 5 in individually and connecting their corresponding retaining means 2, 3 by the spacer device 6, 6', 60, 61, 60b, 61b, 90, 91; or setting a distance of one of several tooth lengths between the interdental matrices 4, 5 and sliding the interdental matrices together in. At a individual sliding in the interdental matrices are fixedly clamped in their retaining means 2, 3. Alternatively, the interdental matrices can be slid in individually and thereafter the retaining means 2, 3 be mounted e.g. by a snap mechanism. The sliding in proceeds for instance by a directly vertical or a reciprocating sawing-like movement.

The pushing apart or relieving of the interdental matrices 4, 5 proceeds for instance by a rotating at the at least one separator screw 6, 6', 60, 61, possibly by a socket wrench.

Several separator screws 6, 6', 60, 61 can be tightened alternately by about 5 revolutions. As soon as the patient experiences a sense of tightness, a small waiting time is observed and thereafter a further tightening by a few more revolutions is made. The tooth spacing which can be arrived at is in a range of about 0.3 Millimeters per interdental space 7, 8. In this range the teeth 110 and 112 can move relatively easy sidewards.

Additional process steps are possible, among others for a preparing and/or finalizing of the above dental medicinal process. The interdental spaces 7, 8 are, for instance, cleaned prior to the inserting of the dental device 1. Smooth tooth surfaces may be cleaned by a fluoride-free cleaning paste and a superfloss. In case of rough surfaces it is also possible to use a fine plastic strip.

The dental medicinal treatment can encompass for instance a prophylactic sealing of a lateral tooth contact surface in the area of an interdental space 7, 8. Thereto, an etching gel is applied during about 120 seconds at a contact area over a large space, which etching gel, for a better wetting of the contact area is possibly distributed and embrocated by massage by a unwaxed dental floss, supersonics or other auxiliary means, whereafter the etching gel is sprayed off after a reaction time span of about 40 seconds, the tooth enamel surface possibly additionally dried by acetone, and thereafter the sealing agent applied over a large area onto the etched contact surface with a penetration time span of about 40 seconds, possibly blown off gently i.e. without any pooling, and cured by application of light of a suitable polymerization lamp led thereto by light wave conductors. The light curing time span amounts to about 1 Minute at a light intensity of about 1000 mW/cm$^2$. Excess material which does not lie on the hardened enamel is thereafter removed by means of a occlubrush or similar. The treated area and its surroundings can, finally, be fluorized.

The tooth treatment process is characterized by following advantages: The interdental spaces 7, 8 can be opened downwards down to the gum. By means of this the corresponding side tooth surface of the not moved tooth 110 can be rendered completely accessible, which is impossible by wedges. A large opening is arrived at atraumatically so that the substances to be applied and also auxiliary means for the improvement of the wetting, dental medicinal tools, etc., are given an excellent access to the entire tooth side surface for its treatment. The opposite side of the tooth 111, 112 which has been pushed away, onto which a interdental matrice 4, 5 rests, is also accessible for the tooth treatment when a interdental matrice 4, 5 with a window 9 is used.

A further dental medicinal treatment concerns a direct restorative filling technique for teeth 110, 111, 112 in the area of the interdental space 7, 8. As described above, a interdental space 7, 8 is spread apart by the dental device 1 structured in accordance with the invention, and thereafter operative process techniques known as such applied at the filling therapy.

In this case the dental device 1 offers considerable advantages. Due to the shrinkage of the polymeric filling material of about 2%–3% it is not or only hardly possible to produce by means of conventional wedges a point of contact between adjacent teeth. Until now a pretension has been produced with the help of the wedge which should compensate the shrinkage. The pretension is, however, hardly controllable and can become oftentimes to small or to high. By means of the dental device 1 it is now for the first time possible to set at the spacer device 6, 6', 60, 61, 60b, 61b, 90, 91 a efficiently defined pretension in such a manner that the desired point of contact is produced at a high reliability.

What is claimed is:

1. Dental device for concurrently enlarging two approximal spaces between three or more teeth, comprising:
   two interdental matrices spaced apart by one or more tooth lengths for insertion into the approximal spaces;
   two retaining means adapted for retaining the interdental matrices in the approximal spaces; and
   wherein at least one of the retaining means is a U-shaped carrier comprising:
      a bases; and
      two side portions with mounting means for mounting a first of the interdental matrices, wherein said side portions hold opposite ends of the first interdental matrix;
   a spacer device engaging the retaining means for pushing the retaining means and for guiding the retaining means parallel, thereby pushing apart the interdental matrices in the approximal spaces, wherein the spacer device modifies a distance between the interdental matrices by increasing the spacing of the approximal spaces between the teeth, and wherein said distance is in a range between at least one tooth length up to a spread length that is larger than one tooth length.

2. Dental device according to claim 1, wherein the interdental matrices are releasably mounted to the retaining means.

3. Dental device according to claim 1, wherein at least one of the interdental matrices includes two partial matrices,
   a first partial matrix held on the retaining means, and
   a second partial matrix held on the first partial matrix.

4. Dental device according to claim 3, wherein both partial matrices include a window common to both.

5. Dental device according to claim 1, wherein the mounting means are clamping jaws with locking screws adapted for engaging perforations in the interdental matrices.

6. Dental device according to claim 5, wherein the U-shaped carrier comprises two U-shaped partial carriers having side portions, wherein the aide portions form the clamping jaws.

7. Dental device according to claim 1, wherein the side portions define insertion slots for mounting the first interdental matrix.

8. Dental device according to claim 7, wherein two opposite edges of the first interdental matrix comprises thickened areas for insertion into the insertion slots.

9. Dental device according to claim 8, wherein the insertion slots comprise snap locks.

10. Dental device according to claim 1, wherein
    a) the spacer device comprises at least one separator screw and at least one guide pin, and
    b) the retaining means comprise at least one threaded bore for the separator screw and at least one guide bore for the guiding pin.

11. Dental device according to claim 1, wherein the dental device comprises a material selected from the group consisting of steel, plastic and a compound material on a carbon fiber basis.

12. Dental device according to claim 1, wherein at least one interdental matrices comprises a window.

13. Dental device according to claim 12, wherein the window comprise a plastic material window or an opening.

14. Dental device according to claim 1, wherein the spacer device is designed in mirror symmetry, having an axis of symmetry common to one of the retaining means.

15. Dental device according to claim 14, wherein one separator screw and a corresponding threaded bore, and one guiding pin and a corresponding guiding bore, are located in a central position or in pair-wise minor symmetrical positions relative to the axis of symmetry.

16. Dental device according to claim 14, wherein either one separator screw and a corresponding threaded bore, or one guiding pin and a corresponding guiding bore, are located in a central position or in pair-wise mirror symmetrical positions relative to the axis of symmetry.

17. Dental device according to claim 1, wherein
    a) the spacer device comprises exactly one separator screw and two guiding pins, or
    b) the spacer device comprises two separator screws and exactly one guiding pin.

18. Dental device according to claim 1, wherein the base comprises a resting surface for supporting a bottom edge of the first interdental matrix.

19. Dental device according to claim 1, wherein the base comprises a projection for providing front-sided or back-sided support of the first interdental matrix against a bending when the retaining means are being pushed apart .

20. Dental device according to claim 1, wherein the dental device is free of sharp edges and is sterilizable.

21. Dental device according to claim 1, wherein the interdental matrices comprise a material selected from the group consisting of steel, plastic, and a compound material on a carbon fiber basis.

22. Dental device for concurrently enlarging two approximal spaces between three or more teeth, comprising:

two interdental matrices spaced apart by one or more tooth lengths for insertion into the approximal spaces:

two retaining means adapted to retaining means adapted for retaining the interdental matrices in the approximal spaces; and a spacer device engaging the retaining means for pushing the retaining means and for guiding the retaining means parallel, thereby pushing apart the interdental matrices in the approximal spaces, wherein the spacer device modifies a distance between the interdental matrices by increasing the spacing of the approximal spaces between the teeth, and wherein said distance is in a range between at least one tooth length up to a spread length that is larger than one tooth length,and wherein the spacer device comprises two separator screws each of which is integrally connected at one end to a guide pin, and wherein a first of the retaining means comprises two threaded bores for the separator screws and a second of the retaining means comprises two guide bores for the guide pins.

23. Dental device according to claim 22, wherein the screws of the dental device are socket head cap screws.

* * * * *